United States Patent
Wimmer et al.

(10) Patent No.: US 6,806,294 B2
(45) Date of Patent: Oct. 19, 2004

(54) OPIOID ANALGESIC

(75) Inventors: Walter Wimmer, Limburg (DE); Bianca Brogmann, Limburg-Eschhofen (DE); Udo Hahn, Nentershausen (DE); Christof Spitzley, Elbtal-Heuchelheim (DE)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 10/128,632

(22) Filed: Apr. 23, 2002

(65) Prior Publication Data

US 2002/0165248 A1 Nov. 7, 2002

Related U.S. Application Data

(63) Continuation of application No. 09/807,492, filed as application No. PCT/EP99/07842 on Oct. 15, 1999, now abandoned.

(51) Int. Cl.[7] .......................... A61K 47/30; A61K 9/20; A61K 9/22; A61K 9/24; A61K 9/28
(52) U.S. Cl. .................... 514/772.3; 424/464; 424/468; 424/472; 424/474
(58) Field of Search ...................... 514/772.3; 424/464, 424/468, 472, 474

(56) References Cited

U.S. PATENT DOCUMENTS

| | | | |
|---|---|---|---|
| 2,738,303 A | 3/1956 | Blythe | 167/82 |
| 3,634,584 A | 1/1972 | Poole | 424/21 |
| 3,845,770 A | 11/1974 | Theeuwes et al. | 128/260 |
| 3,870,790 A | 3/1975 | Lowey et al. | 424/19 |
| 3,916,889 A | 11/1975 | Russell | 128/145.8 |
| 3,916,899 A | 11/1975 | Theeuwes et al. | 128/260 |
| 4,063,064 A | 12/1977 | Saunders et al. | 219/121 L |
| 4,088,864 A | 5/1978 | Theeuwes et al. | 219/121 LM |
| 4,132,753 A | 1/1979 | Blichare et al. | 264/25 |
| 4,377,568 A | 3/1983 | Chopra | 424/31 |
| 4,385,078 A | 5/1983 | Onda et al. | 427/3 |
| 4,389,393 A | 6/1983 | Schor et al. | 424/19 |
| 4,421,736 A | 12/1983 | Walters | 424/19 |

(List continued on next page.)

FOREIGN PATENT DOCUMENTS

| | | | |
|---|---|---|---|
| AU | 9047732 | 7/1990 | |
| AU | 9341654 | 2/1995 | |
| CA | 2082573 | 11/1992 | A61K/47/38 |

(List continued on next page.)

OTHER PUBLICATIONS

Abraham Sunshine et al., "Analgesic Oral Efficacy of Tramadol Hydrochloride in Postoperative Pain," *Clin. Pharmacol. Ther.*, vol. 51, Jun. 1992, pp. 740–746.

E.Beubler, "Medikamentose Schmerztherapie: Kriterien, Moglichkeiten, Risken," *Therapiewoche Osterreich*, 7,2 (1992), pp. 1–15, English translation.

Gourlay, et al., "Influence of a High–Fat Meal On The Absorption of Morphine From Oral Solutions," *Clin. Pharmacol. Ther.*, vol. 46, Oct. 1989, pp. 463–468.

(List continued on next page.)

Primary Examiner—Thurman K. Page
Assistant Examiner—Blessing Fubara
(74) Attorney, Agent, or Firm—Davidson, Davidson & Kappel, LLC

(57) ABSTRACT

The invention is relative to a pharmaceutical preparation, especially for oral administration, with at least one active substance and with formulation components influencing the release of active substance, which preparation comprises at least one opiod analgesic as active substance that is formulated proportionally on the one hand for rapid release and on the other hand for delayed release in such a manner that the in vitro release rate from the preparation according to the Ph. Eur. paddle test shows a mean value of above 40% by weight after one hour and that the in vitro release rate shows a mean value that is still below 80% by weight after four hours.

12 Claims, 1 Drawing Sheet

U.S. PATENT DOCUMENTS

| | | | |
|---|---|---|---|
| 4,443,428 A | 4/1984 | Oshlack et al. | 424/22 |
| 4,464,378 A | 8/1984 | Hussain | 424/260 |
| 4,483,847 A | 11/1984 | Augart | 424/22 |
| 4,520,172 A | 5/1985 | Lehmann et al. | 525/369 |
| 4,548,990 A | 10/1985 | Mueller et al. | 525/123 |
| 4,557,925 A | 12/1985 | Lindahl et al. | 424/19 |
| 4,600,645 A | 7/1986 | Ghebre-Sellassie et al. | 428/403 |
| 4,609,542 A | 9/1986 | Panoz et al. | 424/19 |
| 4,708,874 A | 11/1987 | De Haan et al. | 424/470 |
| 4,728,513 A | 3/1988 | Ventouras | 424/461 |
| 4,797,410 A | 1/1989 | El-Fakahany | 514/356 |
| 4,806,337 A | 2/1989 | Snipes et al. | 71/65 |
| 4,828,836 A | 5/1989 | Elger et al. | 424/419 |
| 4,834,984 A | 5/1989 | Goldie et al. | 424/488 |
| 4,834,985 A | 5/1989 | Elger et al. | 424/488 |
| 4,844,907 A | 7/1989 | Elger et al. | 424/465 |
| 4,844,909 A | 7/1989 | Goldie | 424/480 |
| 4,861,598 A | 8/1989 | Oshlack | 424/468 |
| 4,894,234 A | 1/1990 | Sharma et al. | 424/440 |
| 4,935,246 A | 6/1990 | Ahrens | 424/490 |
| 4,970,075 A | 11/1990 | Oshlack | 424/451 |
| 4,983,730 A | 1/1991 | Domeshek et al. | 536/69 |
| 4,990,341 A | 2/1991 | Goldie et al. | 424/484 |
| 5,007,790 A | 4/1991 | Shell | 424/451 |
| 5,019,397 A | 5/1991 | Wong et al. | 424/473 |
| 5,023,089 A | 6/1991 | Sakamoto et al. | 424/502 |
| 5,024,842 A | 6/1991 | Edgren et al. | 424/473 |
| 5,026,560 A | 6/1991 | Makino et al. | 424/494 |
| 5,030,400 A | 7/1991 | Danielsen et al. | 264/101 |
| 5,068,110 A | 11/1991 | Fawzi et al. | 424/461 |
| 5,071,646 A | 12/1991 | Malkowska et al. | 424/497 |
| 5,122,384 A | 6/1992 | Paradissis et al. | 424/451 |
| 5,126,145 A | 6/1992 | Evenstad et al. | 424/465 |
| 5,132,142 A | 7/1992 | Jones et al. | 427/196 |
| 5,133,974 A | 7/1992 | Paradissis et al. | 424/480 |
| 5,167,964 A | 12/1992 | Muhammad et al. | 424/482 |
| 5,169,645 A | 12/1992 | Shukla et al. | 424/499 |
| 5,178,868 A | 1/1993 | Malmqvist-Granlund et al. | 424/490 |
| 5,196,203 A | 3/1993 | Boehm | 424/469 |
| 5,202,128 A | 4/1993 | Morella et al. | 424/469 |
| 5,206,030 A | 4/1993 | Wheatley et al. | 424/490 |
| 5,213,808 A * | 5/1993 | Bar-Shalom et al. | 424/475 |
| 5,219,575 A | 6/1993 | Van Bommel et al. | 424/490 |
| 5,248,516 A | 9/1993 | Wheatley et al. | 427/3 |
| 5,258,436 A | 11/1993 | Wheatley et al. | 524/388 |
| 5,266,331 A | 11/1993 | Oshlack et al. | 424/468 |
| 5,273,760 A | 12/1993 | Oshlack et al. | 424/480 |
| 5,283,065 A | 2/1994 | Doyon et al. | 424/467 |
| 5,286,493 A | 2/1994 | Oshlack et al. | 424/468 |
| 5,292,461 A | 3/1994 | Juch et al. | 264/37 |
| 5,321,012 A | 6/1994 | Mayer et al. | 514/25 |
| 5,330,766 A | 7/1994 | Morella et al. | 424/490 |
| 5,378,474 A | 1/1995 | Morella et al. | 424/469 |
| 5,384,130 A | 1/1995 | Kamada | 424/461 |
| 5,411,745 A | 5/1995 | Oshlack et al. | 424/456 |
| 5,456,923 A | 10/1995 | Nakamichi et al. | 424/489 |
| 5,460,826 A | 10/1995 | Merrill et al. | 424/470 |
| 5,472,712 A | 12/1995 | Oshlack et al. | 424/480 |
| 5,478,577 A | 12/1995 | Sackler et al. | 424/489 |
| 5,500,227 A | 3/1996 | Oshlack et al. | 424/476 |
| 5,502,058 A | 3/1996 | Mayer et al. | 514/289 |
| 5,508,042 A | 4/1996 | Oshlack et al. | 424/468 |
| 5,520,931 A | 5/1996 | Persson et al. | 424/473 |
| 5,549,912 A | 8/1996 | Oshlack et al. | 424/468 |
| 5,580,578 A | 12/1996 | Oshlack et al. | 424/468 |
| 5,593,695 A | 1/1997 | Merrill et al. | 424/480 |
| 5,601,842 A | 2/1997 | Bartholomaeus | 424/464 |
| 5,614,218 A | 3/1997 | Olsson et al. | 424/456 |
| 5,629,011 A | 5/1997 | Illum | 424/434 |
| 5,637,320 A | 6/1997 | Bourke et al. | 424/489 |
| 5,645,858 A | 7/1997 | Kotwal et al. | 424/495 |
| 5,656,295 A | 8/1997 | Oshlack et al. | 424/468 |
| 5,667,805 A | 9/1997 | Merrill et al. | 424/473 |
| 5,670,172 A | 9/1997 | Buxton et al. | 424/495 |
| 5,672,360 A | 9/1997 | Sackler et al. | 424/490 |
| 5,681,585 A | 10/1997 | Oshlack et al. | 424/494 |
| 5,843,480 A | 12/1998 | Miller et al. | 424/484 |
| 5,849,240 A | 12/1998 | Miller et al. | 264/460 |
| 5,879,705 A | 3/1999 | Heafield et al. | 424/464 |
| 5,891,471 A | 4/1999 | Miller et al. | 424/468 |
| 5,958,459 A | 9/1999 | Chasin et al. | 424/490 |
| 5,965,163 A | 10/1999 | Miller et al. | 424/468 |
| 5,968,551 A | 10/1999 | Oshlack et al. | 424/456 |
| 6,103,261 A | 8/2000 | Chasin et al. | 424/459 |
| 6,143,322 A | 11/2000 | Sackler et al. | 424/459 |

FOREIGN PATENT DOCUMENTS

| | | | |
|---|---|---|---|
| CA | 2131350 | 9/1994 | A61K/31/135 |
| CA | 2229621 | 3/1998 | A61K/31/485 |
| EP | 0097523 | 1/1984 | A61K/9/26 |
| EP | 0108218 | 5/1984 | A61K/9/22 |
| EP | 0147780 | 7/1985 | A61K/9/32 |
| EP | 0235986 | 9/1987 | A61K/9/16 |
| EP | 0253104 | 1/1988 | A61K/9/00 |
| EP | 0267702 | 5/1988 | A61K/9/14 |
| EP | 0271193 | 6/1988 | A61K/31/485 |
| EP | 0327295 | 8/1989 | A61K/9/52 |
| EP | 0361680 | 4/1990 | A61K/9/46 |
| EP | 0361910 | 4/1990 | A61K/9/16 |
| EP | 0377517 | 7/1990 | A61K/31/52 |
| EP | 0377518 | 7/1990 | A61K/9/52 |
| EP | 0388954 | 9/1990 | A61K/9/14 |
| EP | 0377518 | 11/1990 | A61K/9/52 |
| EP | 0415693 | 3/1991 | A61K/37/02 |
| EP | 0430287 | 6/1991 | A61K/9/54 |
| EP | 0452145 | 10/1991 | A61K/9/14 |
| EP | 0576643 | 11/1992 | A61K/9/22 |
| EP | 0532348 | 3/1993 | A61K/31/35 |
| EP | 0533297 | 3/1993 | A61K/9/16 |
| EP | 0534628 | 3/1993 | A61K/31/485 |
| EP | 0535841 | 4/1993 | A61K/31/485 |
| EP | 0546676 | 6/1993 | A61K/9/50 |
| EP | 0553392 | 8/1993 | A61K/9/16 |
| EP | 0580860 | 2/1994 | A61K/9/14 |
| EP | 0624366 | 4/1994 | A61K/31/135 |
| EP | 0631781 | 6/1994 | A61K/31/485 |
| EP | 0609961 | 8/1994 | A61K/31/485 |
| EP | 0642788 | 8/1994 | A61K/31/135 |
| EP | 0624366 | 11/1994 | A61K/31/135 |
| EP | 0636370 | 2/1995 | A61K/31/485 |
| EP | 0642788 | 3/1995 | A61K/31/135 |
| EP | 0665010 | 8/1995 | A61K/9/26 |
| EP | 0864325 | 3/1998 | A61K/9/22 |
| EP | 0 864 325 | * 9/1998 | |
| EP | 2864325 | 9/1998 | A61K/9/22 |
| GB | 2053681 | 2/1981 | A61K/9/22 |
| GB | 2178313 | 2/1987 | A61K/9/14 |
| JP | 04081086 | 4/1992 | A61K/9/10 |
| JP | 0548448 | 6/1993 | A61K/9/50 |
| WO | 2170104 | 7/1986 | A61K/9/58 |
| WO | WO 9201446 | 2/1992 | A61K/9/50 |
| WO | WO9202209 | 2/1992 | A61K/9/22 |
| WO | WO9206679 | 4/1992 | A61K/9/16 |
| WO | WO9208459 | 5/1992 | A61K/31/485 |
| WO | WO9304675 | 3/1993 | A61K/31/16 |
| WO | WO9307859 | 4/1993 | A61K/9/16 |
| WO | WO9307861 | 4/1993 | A61K/9/50 |
| WO | WO9310765 | 6/1993 | A61K/9/22 |
| WO | WO9318753 | 9/1993 | A61K/9/16 |
| WO | WO 9403160 | 2/1994 | A61K/9/32 |

| | | | | |
|---|---|---|---|---|
| WO | WO9403161 | 2/1994 | ............ | A61K/9/52 |
| WO | WO9405262 | 3/1994 | ............ | A61K/9/16 |
| WO | WO9422431 | 10/1994 | .......... | A61K/31/20 |
| WO | WO9600066 | 1/1996 | ......... | A61K/31/485 |
| WO | WO9601629 | 1/1996 | ......... | A61K/31/485 |
| WO | WO9614058 | 5/1996 | ............ | A61K/9/14 |
| WO | 9732573 | 9/1997 | ............ | A61K/9/54 |

OTHER PUBLICATIONS

Geoffrey K. Gourlay, et al. "The Reproducibility of Bio-availability of Oral Morphine from Solution Under Fed and Fasted Conditions," *Journal of Pain and Symtoms Management*,vol. 6., No. 7, Oct. 1991, pp. 431–436.

Robert F. Kaiko, et al., "Controlled–Release Morphine Bioavailability (MS Contin Tablets) in the Presence and Absence of Food," *The Hospice Journal*, vol. 6(4) 1990, pp. 17–30.

Kaiko, et al., "A Single–Dose Study of The Effect of Food Ingestion and Timing of Dose Administration On The Pharmacokinetic Profile of 30–mg Sustained–Release Morphine Sulfate Tablets," *Current Terapeutic Research*, vol. 47, No. 5, May 1990, pp. 869–878.

Yokokawa N., et al., "Relationship between plasma concentration of morphine and analgesic effectiveness," *Postgrad Med J*, (1991) 67 (Suppl. 2) pp. S50–S54.

Physicians Desk Reference 1994, $48^{th}$ Edition, pp. 1821–1824.

D.L. Munday, et al., "Changes in Drug Release Rate 2, Effect of Temperature and Relative Humidity on Polymeric Film Coatings," $5^{th\ Cong.\ Int.\ Tech.\ Pharm}$., 1989, vol. 2, pp. 55–60.

A Protocol for a clinical study entitled "A Randomized, Double–Blind, Parallel–Group Study comparing the Efficacy and Safety of Kapanol® to MS Contin® in the Management of Patients with Moderate to Severe Cancer Pain" ("the Protocol"). The date of the Protocol is indicated as Feb. 10, 1992 and it bears COD No. 14556. The sponsor of the study is indicated to be Faulding Pharmaceuticals, and Australian company.

Certain Patients Diary Cards, Drug Disposition Records, Case Reports Forms and listing which apparently correlates patient randomization number with the treatment of dosing regimen assigned to each patient.

Patient consent forms, apparently for four study participants.

Investigator agreements between the study organizers and certain of the principal investigators.

Abstracts from the Twelfth Annual Congress of the Oncology Nursing Society, May 1987, In Clinical Nursing Forum Supplement vol. 14 (2), p112, 1987.

J. Lapin et al., "Cancer Pain Management with a Controlled Release Oral Morphine Preparation,"*Pain and Symptom Manag.*, vol. 4 (3), pp. 146–151, 1989.

J. Lapin et al., "Guidelines for Use of Controlled Release Oral Morphine in Cancer Pain Management," *Cancer Nursing*, vol. 12 (4), pp. 202–208, (1989).

R.K. Kaiko, "The Pre–and Postoperative Use of Controlled–Release Morphine (MS Contin Tablets): A Review of the Published Literature," Medical Department, The Pudue Frederick Company, Royal Society of Medical Services, International Congress, Symposium Services, No. 149, pp. 147–160 (1989).

H.F. Slowey et al., "Effect of Premedication with Controlled–Release Oral Morphine on Postoperative Pain," Anaesthesia, 1985, vol. 40, pp. 438–440.

MS Contin—Frequency of Daily Dosing, Jan.–Nov. 1990.

R.K. Portenoy, et al., "A Randomized, Double–Blind, Double–Dummy, Crossover Study Comparing the Pharmacolinetics and Pharmacodynamics of Kapanol® Capsules Given Every 24 hours and Every 12 hours with MS Contin® Tablets Given Every 12 Hours in the Management of Patients with Moderate to Severe Chronic Pain" Memorial Hospital IRB Protocol pp. 379–381.

$7^{th}$ World Congress on Pain, Abstracts 997–1001, Aug. 26, 1993.

Advertisement: Roxanol SR., 1988 Roxane Labs, Inc.

T. Hunt and R. Kaiko, Comparison of the Pharmacokinetic Profiles of Two Oral Controlled–Release Morphine Formulation in Healthy Young Adults, *Clin. Thera.*, vol. 13,No. 4, pp. 482–488, 1991.

S. Bloomfield, et al. Analgesic Efficacy and Potency of Two Oral Controlled–Release Morphine Preparations *Clin. Pharmacol. Ther.*, vol. 53, No. 4, pp. 469–478, 1993.

Advertisement: MS Contin 1986, 1987 The Purdue Frederick Company.

Sustained Release Medications, Noyes Data Corp., pp. 3,4, 10–15, 96–99, 335–337 (1980).

Flanders, P., et al. "The Control of Drug Release From Conventional Melt Granulation Matrices," *Drug Development and Industrial Pharmacy*, vol. 13, No. 6, pp. 1001–1022 (1987).

McTaggart, Celia M., et al., "The evaluation of formulation and processing conditions of a melt granulation process," *International Journal of Pharmaceutics*, vol. 19, pp. 139–148 (1984).

Schaefer, T., et al., "Melt granulation in a laboratory scale high shear mixer," *Drug Development and Industrial Pharmacy*, vol. 16, No. 8, pp. 1249–1277 (1990).

Thomsen, L. Juul, et al., "Prolonged Release Matrix Pellets Prepared by Melt Pelletization I. Process Variables," *Drug Development and Industrial Pharmacy*, vol. 19, No. 15, 1867–1887 (1993).

Thomsen, L. Juul, Prolonged Release Matrix Pellets prepared by Melt Pelletization II. Hydrophobic Substances as Meltable Binders vol. 20, No. 77, pp. 1179–1197 (1994).

Thomsen, L. Juul, "Utilizing melt pelletization technique for the preparation of prolonged release products," *Pelletization*, (material elaborated by assistant prof. Lars Juul Thomsen, Department of Pharmaceutics, Royal Danish School of Pharmacy for the DIE course "Pelletization Technologh," Nov. 1992, 106 pages plus 3 appendices.

Thomsen, L. Juul, "Prolonged Release Matrix Pellets Prepared by Melt Pelletization. Part IV: Drug Particles Size, and Binder Composition,":*Pharmaceutical Technology Europa*, pp. 19–24 (Oct. 1994).

Maccarrone C. et al.; Single Dose Pharmacokinetics of Kapanol™, a New Oral Sustained–Release Morphine Formulation; *Clinical Drug Investigation* 1994:7 (5) 262–274.

West R. J., et al., "Single dose pharmacokinetics of a new oral sustained release morphine formulation, Kapanol™ capsules," (Abstract 997) International Association for the Study of Pain, $7^{th}$ World Congress on Pain. Paris, Aug. 22–27, 1993 (Data on file, Glaxo Australia, F.H. Faulding).

Gourlay GK, et al., "A comparison of Kapanol™ (A new sustained release morphine formulation), MST Contius® and morphine solution in cancer patients: pharmacokinetics aspects." (Abstract 998) International Association for the Study of Pain, $7^{th}$ World Congress on Pain Paris, Aug. 22–27, 1993 (Data on file, Glaxo Australia, F.H. Faulding).

Cherry DA, et al., "A comparison of Kapanol™ (a new sustained release morphine formulation), MST Continus® and morphine solution in cancer patients: Morphine metabolite profiles and renal function." (Abstract 999) International Association for the Study of Pain, 7th World Congress on Pain, Paris Aug. 22–27, 1993 (Data on file, Glaxo Australia, F.H. Faulding).

Plummer JL, et al., "A comparison of Kapanol™ (a new sustained release morphine formulation) MST Continus® and mophine solution in cancer patients: pharmcodynamic aspects." (Abstract 1000) International Association for the Study of Pain, 7th World Congress on Pain, Paris, Aug. 22–27, 1993 (Data on file, Glaxo Australia, F.H. Faulding).

Toner G, Cramond T, Bishop, et al., "Randomized double blind, phase III crossover study of a new sustained–release oral mophine fornulation, Kapanol™ capsules", (Abstract 1001) International Association for the Study on Pain, Paris, Aug. 22–27, 1993 (Data on file, Glaxo Australia, F.H. Faulding).

Cherry DA, et al., "Once a Day (i.e. 24 Hourly) Kapanol™, A New Sustained Release Morphine Formulation, in the Treatment of Cancer Pain: Morphine Metabolite Profiles"; European Journal of Cancer; Part A General Topics 1995; 31 (S5) Suppl:S184 Abs 884, European Conference on Clinical Oncology and Cancer Nursing, Paris, Oct. 29–Nov. 2, 1995.

Gourlay, et al.,; "Once A Day (i.e. 24 Hourly) Kapanol™, A New Sustained Release Morphine Formulation, In The Treatment of Cancer Pain: Pharmacokinetic Aspects", European Journal of Cancer; Part A General Topics 1995:31 (S5) Suppl: S187 Abs 897, European Conference on Clinical Oncology and Cancer Nursing, Paris, Oct. 29–Nov. 2, 1995.

Broomhead, et al. "Kadian™/Kapanol™–A Once Daily Morphine Formulation" European Journal of Cancer; Part A General Topics 1995:31 (S5) Suppl: S182 Abs 873, European Conference on Clinical Onclology and Cancer Nursing, Paris, Oct. 29–Nov. 2, 1995.

Gourlay et al., Proceedings of the 7th World Congress on Pain; A comparison of Kapanol (a New Sustained–Release Morphine Formulation), MST Continus, and Morphine Solution in Cancer Patients: Pharmacolinetic Aspects of Morphine and Morphine Metabolites Progress in Pain Research and Management vol. 2 pp 631–643.

Kaiko R.F., "Clinical Protocol and Role of Controlled Release Morphine in the Surgical Patient," *Anesthesiology and Pain Management* 1991 pp 193–212.

MS Contin—Frequency of Daily Dosing (NDTI)—Jun., 1991–May, 1992.

* cited by examiner

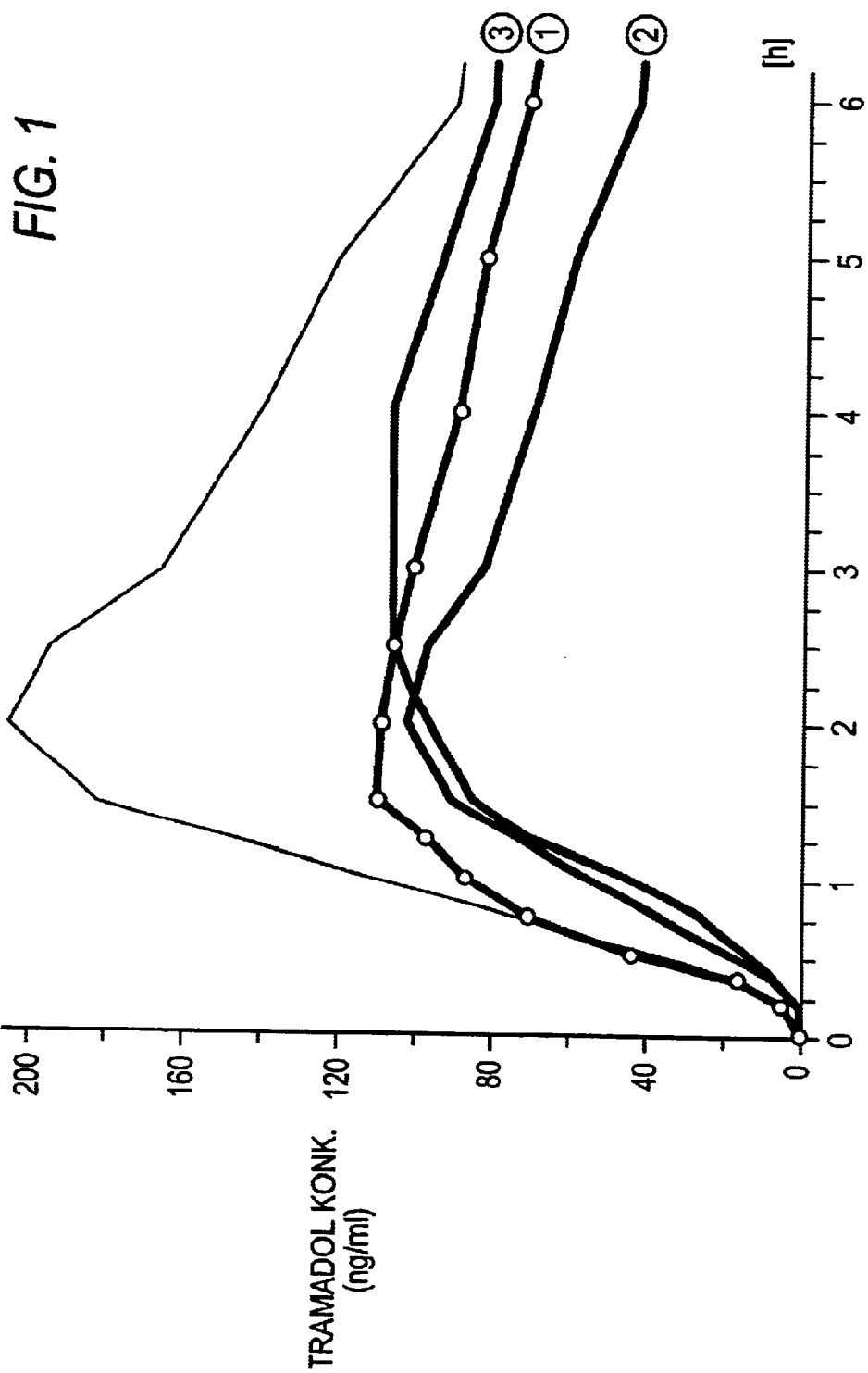

OPIOID ANALGESIC

This application is a CONTINUATION of U.S. patent application Ser. No. 09/807,492 filed Apr. 13, 2001, now abandoned which is a national stage of PTC/EP99/07842 filed Oct. 15, 1999 the disclosure of which is hereby incorporated by reference.

The invention is relative to a pharmaceutical preparation, especially for oral administration, with at least one active substance and with formulation components influencing the release of active substance, which preparation comprises at least one opiod analgesic as active substance that is formulated proportionally on the one hand for rapid release and on the other hand for delayed release. The invention is especially relative to pharmaceutical preparations containing tramadol or a pharmaceutically compatible salt of tramadol, especially tramadol hydrochloride, as active substance.

So-called "multiphase" pharmaceutical preparations in which the active-substance content is formulated on the one hand for a rapid release and on the other hand for a delayed (retarded) release have long been known. Such preparations have also already been frequently described for analgesics.

EP-A 0,243,366 teaches a sustained-[controlled-]release formulation for tramadol that is suitable for a uniform and long-lasting release of the active substance over twenty-four hours or longer.

EP-A1 0,642,788 teaches pharmaceutical preparations in tablet form containing a tramadol salt as active substance that is present in a matrix for the delayed release of active substance. Cellulose ether[s] and/or cellulose ester[s] are an essential component of this matrix and exhibit a viscosity between 300 and 150,000 mPas in a 2% by wt. aqueous solution at 20° C. It is pointed out in the specification that the tablet core, that contains the matrix containing the active substance, can be encased with additional active substance that is not delayed and is therefore rapidly released. Multilayer tablets and laminated tablets are cited as examples.

Multiphase tramadol preparations art commercially available. The product "Tramadolor ID 100" of Hexal AG, that contains tramadol on the one hand in sustained-release formulation and on the other hand in a rapid-release formulation is an example thereof. However, the in vitro release data as well as the blood plasma level development in time correspond to a relatively slow initial flooding, so that the start of the desired analgesic action after administration of the preparation does not always take place as rapidly as would be desired.

EP-A2 0,864,325 recently disclosed another two-phase preparation containing an opiod analgesic, e.g., tramadol hydrochloride, in sustained-release and rapid release formulation. According to this publication the in vitro release rate (determined according to the paddle test described in Ph. Eur.) is extremely high; at least 50% by wt. of the active substance is released from the preparation within one hour in vitro. The examples of EP-A2 0,864,325 even correspond in part to much greater release rates: After two hours approximately 70% by wt. and after four hours approximately 90% by wt. of the active substance has been released and after six hours the release of active substance is practically concluded.

This corresponds to an extremely rapid buildup of a high plasma level of the active substance and to a correspondingly very rapidly beginning analgesic action.

However, it is indicated on the other hand in EP-A2 0,864,325 that after a one-time application under fasting conditions blood plasma levels of 90 to 200 ng/ml and in the preferred range blood plasma levels of far above 100 ng/ml were still found after five hours.

The active-substance dosage applied in a one-time manner to which this blood plasma level development corresponds is not indicated in the application. However, it can be deduced from a consideration of the magnitude [size], that such high plasma level values after five hours are only possible, in view of the extremely rapid total release of the active substance from the preparation, if the dosing of the active substance in the unit [standard] dosage is very high. The data in EP-A2 0,864,325 probably corresponds to a unit dose of 200 mg active substance. Since a twice daily application is provided, the maximum daily dose of 400 mg given in the tramadol monograph of the Federal Health Office dated 1994 is not exceeded (but is reached) at such a high amount of active substance in the unit dose; however, this also means that the patient is exposed for hours to a very high concentration of active substance in the time between the first attainment of the analgetically active concentration on the one hand and the dropping of the plasma level below the analgetically active concentration on the other hand, which very high concentration of active substance is far above that necessary for analgetic action.

On the other hand, it also follows from the data of this application that the action in the sense of a freedom from pain in the patient can not last twelve hours. The very rapid total release of the active substance also corresponds to a correspondingly short half-life $W_{50}$. Thus, in the case of a twice-daily administration the patient is supplied with too much active substance for hours and subsequently with too little active substance for several hours.

In view of this state of the art, a significant problem of the invention is to create a pharmaceutical preparation of the initially cited type that combines the most rapid possible start of the analgetic action with the longest possible duration of action while avoiding high plasma concentrations of the active substance in the interim.

The invention has the further significant problem of creating such a preparation of the initially cited type that makes possible a uniform and sufficiently analgetic action over the entire 24-hour period at a dosage of twice to three times daily.

Further problems and advantages of the invention result from the following description.

Preparations preferred in accordance with the invention comprise as active substance at least an opiod analgesic, preferably bupivacaine, buprenorphine, clofenadol, codeine, dextromoramide, diamorphine, dihydrocodeine, dihydromorphine, ethylmorphine, fentanyl, hydrocodone, hydromorphone, levomethadone, meperidine, methadone, morphine, nalbuphine, nefopam, normethadone, oxycodone, oxymorphone, pentazocine, pethidine, phenpyramide, piritramide, propoxyphene, tebacone, tilidine, tramadol and/or their physiologically compatible salts as well as derivatives of the previously cited active substances.

The invention basically solves the problem, according to the features of the independent claims, with the formulation of the pharmaceutical preparation in such a manner that the opioid analgesic contained in the preparation, in particular a tramadol salt such as tramadol hydrochloride, is in part formulated for a rapid release and in part for a delayed release in such a manner that the in vitro release rate from the preparation according to the paddle test in accordance with Ph. Eur. shows a mean value [an average value] of more than 40% by wt. already after one hour but on the other hand 80% by wt. active substance had not yet been achieved after four hours under the same test conditions.

In a preferred embodiment of the invention more than 70% by wt. of the active substance has already been released after four hours in vitro. After seven to ten hours, and especially preferably after approximately eight hours approximately 90% by wt. of the active substance has been released in vitro. However, it is preferable if a complete release has not yet been achieved after fourteen hours, in particular not yet after sixteen hours.

In comparison to EP-A2 0,864,325, the initial course of the release up to approximately one hour is similar. The release after one hour attains 40% by wt. in every instance but must not attain the 50% by wt. prescribed in the state of the art. However, it is possible and is also preferred if the release in vitro has a mean value of approximately 50% by weight or even more according to the mentioned paddle test.

This can be achieved by appropriately adjusting the release rate. To this end, especially the type and amount of the disintegrant worked into the rapid-release component of the preparation is to be used. In principle, the amount of active substance released within the first hour in the agent in the paddle test can be increased by increasing the amount of disintegrant. Disintegrants suitable in accordance with the invention preferably comprise a polymer and especially preferably cross-linked polyvinylpyrrolidone (PVP).

The release curve then differs very clearly from the teaching of EP-A2 0,864,325 especially in the time after two hours after administration. The release takes place, substantially from the sustained-release component of the preparation, very much slower and up to approximately the complete release a preferred preparation in accordance with the invention takes more than twice as long (more than sixteen hours in comparison to approximately eight hours) as according to EP-A2 0,864,325.

The principle of the invention can also be defined via the plasma levels of the active substance, that are measured after a one-time administration of a preparation of the invention in the agent using a plurality of test subjects. The development in time of the plasma level of the active substance for a preparation in accordance with the invention is approximately as follows:

These values refer to the one-time administration of a dose of 100 mg of the analgesic, especially tramadol hydrochloride. The absolute values of the plasma level are naturally dependent on the given dose. However, the development in time of the plasma level corresponds substantially to the above values even in the case of other one-time dosages than 100 mg analgesic as regards their curve shape, taking appropriate account of the different dosing.

Preparations in accordance with the invention make possible an average half-life $W_{50}$ (relative again to a one-time application of 100 mg active substance) of more than five hours, preferably of more than six hours and especially preferably more than seven hours.

The pharmaceutical preparations of the invention contain at least one active substance and their active-substance component contains at least one opiod analgesic. Pharmaceutical preparations of the invention can also contain more than one opiod analgesic and can also contain other active substances in addition to one or more opiod analgesics. Other active substances that can be combined with opiod analgesics are known in the state of the art.

The analgesics that can be contained in the preparations of the invention correspond to the active substances indicated in the initially cited state of the art, in particular to the opiod analgesics cited in EP-A2 0,864,325. Tramadol, especially in the form of tramadol hydrochloride, is especially preferred as active substance.

The analgesic active substance, especially preferably an opiod, is preferably distributed in a nonuniform manner onto the two "phases" of the preparation, that release at different rates, in such a manner that the relatively greater part of the active substance is formulated for delayed release. Generally speaking, therefore, the amount of the analgesic in the rapidly releasing phase of the preparation is less than 50% and the amount of the active substance in a sustained-release matrix is greater than 50% relative to the total content of analgesic active substance in the preparation. It is especially preferable if the relative amounts of the active substance in

| At least | 2 ng/ml | Preferably at least | 3 ng/ml | Especially preferably at least | 4 ng/ml | after 0.15 h |
|---|---|---|---|---|---|---|
| " | 10 ng/ml | Preferably at least | 13 ng/ml | Especially preferably at least | 15 ng/ml | after 0.30 h |
| " | 35 ng/ml | Preferably at least | 40 ng/ml | Especially preferably at least | 45 ng/ml | after 0.50 h |
| " | 55 ng/ml | Preferably at least | 60 ng/ml | Especially preferably at least | 65 ng/ml | after 0.75 h |
| " | 75 ng/ml | Preferably at least | 80 ng/ml | Especially preferably at least | 85 ng/ml | after 1.0 h |
| " | 85 ng/ml | Preferably at least | 90 ng/ml | Especially preferably at least | 95 ng/ml | after 1.25 h |
| " | 100 ng/ml | Preferably at least | 105 ng/ml | Especially preferably at least | 110 ng/ml | after 1.5 h |

The further development in time then corresponds to the following:

| Plasma concentration | Time after administration |
|---|---|
| between 90 and 120 ng/ml | between 2 h and 4 h |
| between 60 and 100 ng/ml | between 4 h and 8 h |
| between 40 and 60 ng/ml | between 8 h and 11 h and |
| in particular above 30 ng/ml up to 16 h after administration. | | the rapid-release "phase" and in the delayed-release "phase" of the tablets are in the approximate ratio of 1:3 to 1:5. This corresponds in a tablet in accordance with the invention with a total of 100 mg tramadol hydrochloride and at a ratio of 1:3 to a distribution of 25 mg tramadol hydrochloride in the rapid-release component and 75 mg tramadol hydrochloride in the delayed-release component of each tablet.

Whereas the preferred unit dose of the analgesic, especially for tramadol hydrochloride, is approximately 100 mg, it can deviate from this. The active-substance content of a preparation in accordance with the invention is generally between 20 and 500 mg, especially between 50 and 200 mg in a unit dose. High dosages are less preferable since the invention makes it possible to combine a rapid flooding with a long-lasting duration of action without the maximum concentration of active substance in the blood of the patient reaching undesirably high values.

The preparations of the invention are preferably solid medicinal forms. Tablets, especially bilaminar tablets are especially preferred. The delayed-release component of the analgesic, preferably an opiod, is then located in one layer whereas the rapid-release component is taken up in the other layer. The tablet is then preferably provided with an external coating that imparts properties to it that are on the whole neutral in taste.

The rapid-release part of the pharmaceutical preparation of the invention comprises a potent disintegrant formed in particular from a polymer. At the present, a cross-linked PVP is especially preferable. The amount of disintegrant in the rapid-release part of the preparation must be dimensioned in such a manner that the desired rapid release and therewith the rapid flooding of the active substance are achieved. The amount of disintegrant therefore corresponds to at least 10% by weight of the total mass (including the amount of active substance) of the rapid-release "phase" of the preparation. Often, the amount corresponds to at least 20% by weight, preferably at least 25% by weight and especially preferably at least 30% by weight, relative again to the mass of the part of the preparation of the invention constituting the formulation of the rapid-release active substance. In order to achieve an specially strong flooding and a corresponding, initial release of active substance, the amount of disintegrant can also be above 30% by weight; in an especially preferred embodiment of the invention it is approximately 32% by weight, relative again to the same basis.

In addition to the cited amount of disintegrant, cross-linked PVP in particular, such a rapid-release formulation in accordance with the invention also contains the rapid-release amount of the active substance, e.g., 25 mg tramadol hydrochloride in a 100 mg tramadol tablet. Furthermore, the rapid-release formulation preferably contains a lactose hydrate such as, in particular, lactose monohydrate, whose amount can also be up to approximately 30% by weight relative to the total mass of the rapid-release part of the preparation.

Further components such as, e.g., binders (preferably polyvidone), magnesium stearate and the like can be added in customary amounts. The rapid-release component of the preparation contains a small amount (approximately 1 mg) purified water in addition in the most-preferred embodiment.

The sustained-release matrix, that is provided, e.g., in the second layer of a bilaminar tablet in accordance with the invention, basically corresponds to the sustained-release matrixes for opiod analgesics such as tramadol in particular, which matrixes are already known in the state of the art. They can be formed in accordance with EP-A1 0,624,366 (already cited). The compounds indicated in it can also be used as sustained-release matrix for the present invention either in general or as an exemplary embodiment.

For example, in a currently especially preferred embodiment the compound of a preparation in accordance with the invention formulated for delayed release contains a mixture of lactose monohydrate, ethylcellulose with low viscosity and cetostearyl alcohol as main components in addition to the appropriate amount of active substance (thus, 75 mg active substance, especially tramadol hydrochloride in a 100 mg tablet). In addition, other formulation aids can be added that are known in the state of the art.

The production of preparations in accordance with the invention takes place according to methods known and described in the state of the art. For example, tablets in the sense of preparations in accordance with the invention can be produced according to the methods described in EP-B1 0,642,788 (already cited).

An especially important indication for preparations in accordance with the invention is acute pain therapy. Such preparations can be used with particular advantage in this instance instead of the currently customary drops on account of the rapid and high flooding.

A currently especially preferred embodiment of the invention is described by way of example in the following.

EXAMPLE

A preparation in accordance with the invention is produced in that at first a sustained-release matrix is formed substantially from approximately 50 mg lactose monohydrate, approximately 8 mg ethyl cellulose and approximately 32 mg cetostearyl alcohol, plus approximately 2 mg talcum, approximately 1.5 mg magnesium stearate, approximately 1 mg oleic acid, approximately 1.7 mg dibutylsebacate and approximately 2 mg water. 75 mg tramadol hydrochloride are worked into this sustained-release matrix in a known manner. The sustained-release matrix containing the active substance is added as a layer for a bilaminar tablet.

A rapid release formulation is produced in parallel from 25 mg tramadol hydrochloride, 27.5 mg lactose monohydrate, 1 mg magnesium stearate, 4.25 mg polyvidone, 27.5 mg microcrystalline cellulose and approximately 1 mg water. The addition and mixing of the components also takes place here according to methods known in the state of the art.

The mass containing the sustained-release matrix with the main mass of the active substance is then processed in a known manner with the rapid-release formulation containing the active substance to a bilaminar tablet.

The tablet formed in this manner is then provided with a coating containing as main component hydroxypropylmethylcellulose, polydextrose, Macrogol4000 and talcum. The tablet is neutral in taste as a result of this coating and can be more easily swallowed.

The total mass of the tablet is approximately 290 mg with a total content of tramadol hydrochloride of 100 mg distributed in a ratio of 75:25 in the sustained -release matrix layer and the rapid -release layer of the tablet.

The tramadol plasma level values were measured in their development over time in a plurality of test subjects with the tablets described in the example. Twenty-four healthy male test subjects took part in the test. The test was designed as an open, randomized crossover test in single-dose administration. A pause (as washout) of one week was present between each two tests.

The test subjects received the preparations Tramundin®, a capsule preparation with 50 mg tramadol hydrochloride and rapid release and Tramundin® sustained-release with 100 mg tramadol hydrochloride in a sustained-release formulation, which preparations have been commercially available for some time and correspond, e.g., to EP-A1 0,624,366 for a comparison with the tablets indicated in the example.

The taking of blood for determining the plasma values took place before the administration and at the intervals in time in the following table 1.

TABLE 1

| | Plasma level (ng/ml) | | |
| --- | --- | --- | --- |
| Time (h) | Tramundin SL | Tramundin | Sustained-release Tramundin |
| 0.00 | 0.00 | 0.00 | 0.00 |
| 0.17 | 4.98 | 1.57 | 1.32 |
| 0.33 | 16.44 | 7.05 | 7.82 |
| 0.50 | 46.02 | 19.20 | 15.38 |
| 0.75 | 69.11 | 40.03 | 30.04 |
| 1.00 | 87.53 | 54.57 | 45[?].95 [illeg.] |
| 1.25 | 97.97 | 74.74 | 67.78 |
| 1.50 | 110.53 | 89.44 | 85.57 |
| 2.00 | 109.27 | 103.14 | 96.58 |
| 2.50 | 106.58 | 97.78 | 108.10 |
| 3.00 | 100.65 | 83.76 | 107.77 |
| 4.00 | 92.25 | 69.84 | 106.18 |
| 5.00 | 85.54 | 61.28 | 95.37 |
| 6.00 | 74.02 | 48.41 | 86.21 |
| 8.00 | 64.22 | 41.22 | 77.78 |
| 10.00 | 52.40 | 31.56 | 68.32 |
| 12.00 | 40.22 | 24.62 | 53.48 |
| 18.00 | 29.83 | 14.32 | 37.77 |
| 24.00 | 14.75 | 7.40 | 18.32 |
| 36.00 | 4.80 | 1.63 | 6.76 |

"Tramundin SL" is the two-phase tablet in accordance with the invention and described in the example.

The initial flooding, that is distinctly more rapid in comparison to the known tramadol formulations, as well as the long-lasting maintenance of relevant plasma levels can be recognized from the development of the plasma levels. This is shown graphically in attached FIG. 1 in which the curve designated with 1 corresponds to the "two-phase" preparation Tramundin SL in accordance with the invention already described in the above example. The curve designated with 2 corresponds to the preparation Tramundin, that is, the rapid-release capsule and the curve designated with 3 comprises the values for sustained-release Tramundin as indicated above. In addition, there is a curve sketched in with a thin line that corresponds to a recalculation of the values of curve No. 2 at an active-substance content of 100 mg tramadol hydrochloride.

It can be directly seen from the numeric values indicated as well as from FIG. 1 that the preparation in accordance with the invention exhibits a very rapid flooding such as would otherwise only be obtainable in a preparation with on the whole rapid release, which would, however, result in very high $C_{max}$ values, and combines this with a very long-lasting action that is clearly superior to non-delayed [retarded] formulations and almost attains the values of the known formulation of Tramundin, that is only delayed [retarded]. Thus, a desired, rapid flooding is united with a very great half-life without the patient being exposed to unnecessarily high concentrations of active substance between the start and the subsidence.

What is claimed is:

1. A pharmaceutical preparation for oral administration comprising a bilaminar tablet comprising a rapid release layer comprising tramadol or a pharmaceutically acceptable salt thereof, polyvinylpyrrolidine and microcrystalline cellulose; and a delayed release layer comprising tramadol or a pharmaceutically acceptable salt thereof, ethylcellulose, and cetostearyl alcohol said preparation exhibiting an in vitro release rate according to the Ph. Eur. paddle test of a mean value of above 40% by weight after one hour and a mean value of below 80% by weight after four hours.

2. The preparation according to claim 1, characterized in that the release rate is above 70% by weight after four hours.

3. The preparation according to claim 1, wherein the release rate is below 100% by weight after fourteen hours.

4. The pharmaceutical preparation for oral administration of claim 1, wherein the preparation provides a plasma level of the tramadol of at least 2 ng/ml after 0.15 h, at least 10 ng/ml after 0.30 h, at least 35 ng/ml after 0.50 h, at least 55 ng/ml after 0.75 h, at least 75 ng/ml after 1.0 h, at least 85 ng/ml after 1.25 h and at least 100 ng/ml after 1.50 h based on a one-time administration of 100 mg.

5. The pharmaceutical preparation according to claim 4, wherein the preparation provides a plasma level of the tramadol of between 90 ng/ml and 120 ng/ml between 2 h and 4 h; between 60 ng/ml and 100 ng/ml between 4 h and 8 h; and between 40 ng/ml and 60 ng/ml between 8 h and 11 h, based on a one-time administration of 100 mg.

6. The preparation according to claim 4, wherein the tramadol is in the form of tramadol hydrochloride.

7. The preparation according to claim 4, wherein the preparation comprises between 20 and 500 mg tramadol hydrochloride per unit dose.

8. The preparation according to claim 4, wherein the ratio of the tramadol between the rapid-release layer and the delayed-release layer is from about 3:1 to about 5:1.

9. The preparation according to claim 1, further comprising a coating that is neutral in taste.

10. The preparation according to claim 1, wherein the tramadol is in the form of tramadol hydrochloride.

11. The preparation according to claim 1, wherein the ratio of the tramadol between the rapid-release layer and the delayed-release layer is from about 3:1 to about 5:1.

12. The preparation according to claim 1, characterized in that the preparation is formed as a tablet and is provided with a coating that is neutral in taste.

\* \* \* \* \*